United States Patent [19]

Möller

[11] Patent Number: 4,728,604

[45] Date of Patent: Mar. 1, 1988

[54] PROCESS AND REAGENT FOR THE DETERMINATION OF TRANSAMINASE

[75] Inventor: Gerald Möller, Tutzing, Fed. Rep. of Germany

[73] Assignee: Boehringer Mannheim GmbH, Mannheim, Fed. Rep. of Germany

[21] Appl. No.: 642,423

[22] Filed: Aug. 20, 1984

[30] Foreign Application Priority Data

Aug. 22, 1983 [DE] Fed. Rep. of Germany ....... 3330246

[51] Int. Cl.$^4$ .................. C12Q 1/52; C12Q 1/32; C12R 1/01; C12R 1/225; C12R 1/25
[52] U.S. Cl. .................. 435/16; 435/26; 435/853; 435/857; 435/822; 435/810
[58] Field of Search .............. 435/16, 26, 853, 857, 435/190, 810, 822

[56] References Cited

U.S. PATENT DOCUMENTS 3,527,332 9/1970 Deutsch ........................ 435/16
3,819,488 6/1974 Rush et al. ..................... 435/16

OTHER PUBLICATIONS

*Enzyme Nomenclature* (1972), American Elsevier Publishing Co., Inc., N.Y., pp. 46-47.
Gawehn et al., "Chemical Abstracts", vol. 82 (1975), Abstract #28119n.
*The Prokaryotes*, Starr et al. (eds.), vol. II (1981), Springer-Verlag, N.Y., pp. 1626-1627 and 1671.

*Primary Examiner*—Esther M. Kepplinger
*Attorney, Agent, or Firm*—Felfe & Lynch

[57] ABSTRACT

For the determination of the transaminasae by reaction of a corresponding amino acid with α-ketoglutaric acid to form glutamate and the α-keto acid corresponding to the amino acid used, and measurement of the α-ketonic acid formed by reduction in the presence of lactate dehydrogenase (LDH) and optionally of malate dehydrogenase (MDH) with NADH, forming NAD+ and α-oxy acid, use is made of D-LDH from lactic acid bacterium.

13 Claims, 1 Drawing Figure

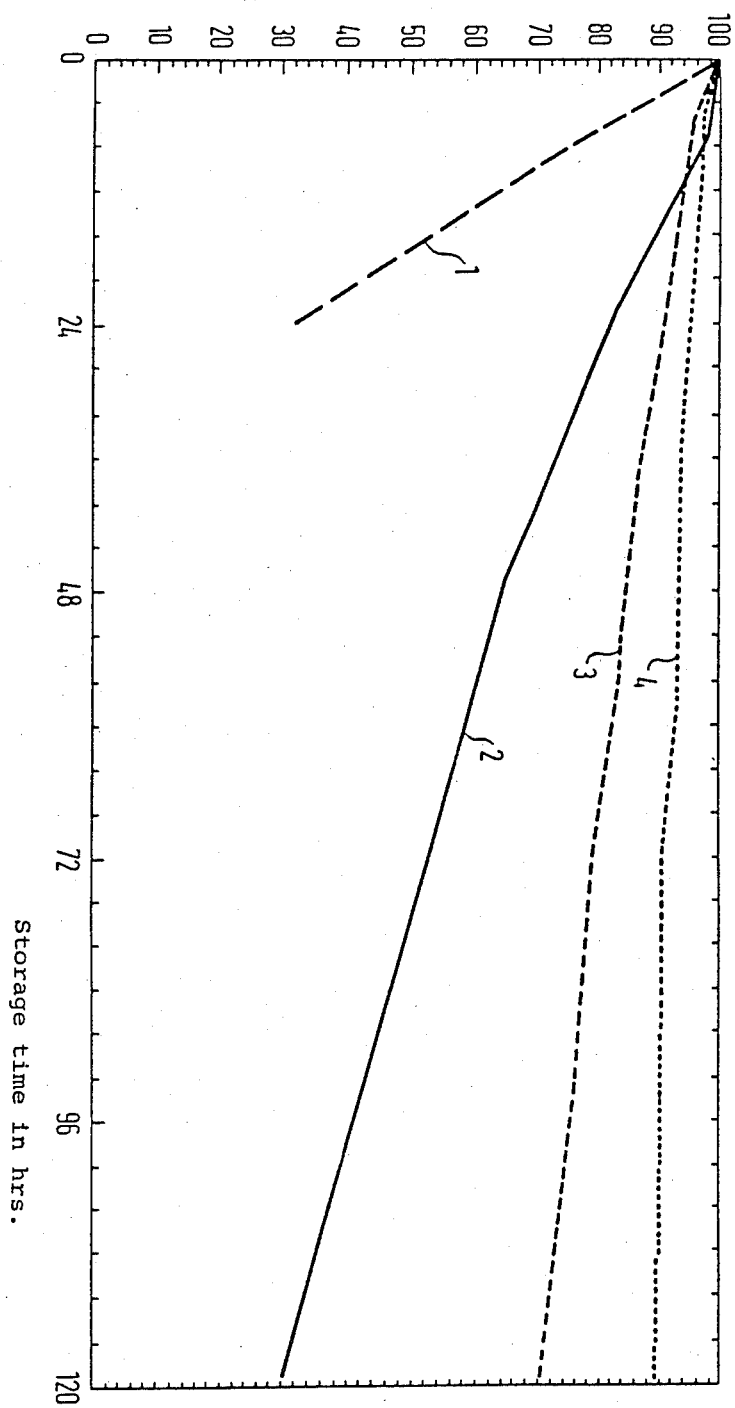

PROCESS AND REAGENT FOR THE DETERMINATION OF TRANSAMINASE

Human tissue contains the tranaminasae glutamatepyruvate-transaminase(GPT) EC 2.6.1.2 and glutamateoxalacetate-transaminase(GOT) EC 2.6.1.1 in muscles, serum and in the organs. The measurement of the GPT content, especially in serum, represents an important clinical parameter for the differentiation of liver and heart diseases.

The GPT is almost execlusively present in the liver, where it is only present in the cytoplasma of the parenchyma cells, whereas the GOT(glutamate-oxalacetate-transaminase) is present as to about 50% in the cytoplasma and in the mitochondria. This localization of the two transaminasae provides valuable diagnostic indications for various liver diseases. Higher GOT values are evidence of serious damage to the liver parenchyma cells.

In the case of acute hepatitis GOT and GPT are always increased in the serum, even in the anicteric development. Often one can prove the enzyme activity increase before the appearance of the icterus.

With chronic hepatitis and cirrhosis, GOT and GPT are lower than in the case of virus hepatitis. Their determination is valuable primarily with chronic liver inflammation for the supervision of the course of the illness and for the therapy.

The determination of the GOT is also used for diagnosis of diseases of the heart muscles.

A conventional and much-used process for the determination of GPT/GOT employs the transamination of α-keto-glutaric acid with alanine and/or aspartate which is catalysed by this enzyme and leads to the formation of glutamate and pyruvate or oxalacetate. Pyruvate or oxalacetate is reacted by the reduction with NADH in the presence of lactate dehydrogenase(LDH) and optionally of MDH into lactate or malate and NAD$^+$, wherein the latter is measured according to the prior art methods either directly in UV or with the aid of a subsequent color reaction.

An important disadvantage of this process is that LDH itself has a non-specificity (side effect) which leads to a reaction of α-ketonic acids, especially of α-ketonic glutaric with the formation of α-hydroxyglutaric acid and can be designated as α-hydroxy-glutarate dehydrogenase activity.

This non-specificity moreover has the result that a corresponding reagent for the known process has inadequate stability, since with the formation of α-hydroxyglutarate, NADH is oxidized into NAD. This causes a slow reaction.

The invention is based on the object of solving this problem.

Inventively this is achieved in a process for the determination of transaminasae by reaction of a corresponding amino acid with α-ketoglutaric acid to form glutamate and the α-ketonic acid corresponding to the amino acid used and measurement of the α-ketonic acid thus formed by reduction with NADH in the presence of lactate dehydrogenase (LDH) and optionally of malate dehydrogenase(MDH) forming NAD$^+$ and α-oxyacid, which is characterized in that D-LDH is used of a lactic acid bacterium.

The invention is based on the surprising discovery that D-LDH of lactic acid bacteria is not reduced in the presence of NADH α-oxoglutaric acid. If we therefore replace the conventionally used LDH from porcine hearts in the above-named process according to the invention by D-LDH of a lactic acid bacterium, the troublesome slow reaction no longer appears and a substantially improved reagent with respect to storage life is obtained.

The advantageous results of the invention are obtained with any D-LDH of lactic acid bacteria. Lactic acid bacteria forming D-LDH belong in the main to the strains lactobacillus, pediococcus, and leuconostoc (Antonie van Leeuwenhoek 49, 1983, 210). To the extent that lactic acid bacteria from L-LDH, it is unsuitable. In so far as a strain forms both D-LDH and L-LDH, a separation of the two enzymes must be effected. Preferably therefore D-LDH preparations from strains which contain only D-LDH are used. Especially good results have been provided by LDH from *lactobacillus leichmannii*, DSM 2699, which is a D-LDH. Further preferred strains include lactobacillus lactis, DSM 20072, *lactobacillus plantarum*, DSM 20174, *leuconostoc mesenteroides* DSM 20193 or *pediococcus pentosaceus* DSM 20280.

If the inventive process is used for the determination of the glutamate-pyruvate-transaminase(GPT), alanine is used as the amino acid, which disaminates into pyruvate and is then reduced to lactate.

If it is used for the determination of glutamateoxalacetate-transaminase(GOT), aspartate is used as the amino acid, which disaminates into oxalacetate and is then reduced to malate.

An inventive reagent for the determination of transaminasae containing LDH, α-oxoglutarate, the corresponding amino acid, NADH, buffer pH 6.5 to 8.5 and optionally MDH is therefore distinguished by the fact that it contains D-LDH of a lactic acid bacterium.

In the case of GPT determination, the reagent contains alanine as the amino acid. In the case of GOT determination, it contains aspartate as the amino acid and in addition malate dehydrogenase(MDH).

A preferred embodiment of the inventive reagent contains for determination of GPT:
250 to 20,000 U/l D-LDH of lactic acid bacteria
2.5 to 100 mmol/l of alanine,
0.01 to 0.25 mmol/l NADH and
10 to 500 mmol/l buffer with pH from 6.5. to 8.5.

Another preferred embodiment for determination of GOT by the inventive reagent contains:
250 to 20,000 U/l D-LDH of lactic acid bacteria,
2.5 to 100 mmol/l α-oxoglutarate,
20 to 1000 mmol/l aspartate,
0.01 to 0.25 mmol/l NADH and
10 to 500 mmol/l buffer with pH from 6.5 to 8.5.

Within the scope of the invention, the specially preferred final concentration of the individual components of the GPT buffer in the test are: LDH 1000 to 1400 U/l, alanine 600 to 800 mmol/l, NADH 0.10 to 0.20 mmol/l, α-oxoglutarate 10 to 25 mmol/l and buffer 50 to 100 mmol/l pH 7.3 to 7.5.

The corresponding values for concentration in the test with the GOT reagent are 1000 to 1400 U/l LDH, 500 to 1000 U/l MDH, 0.10 to 0.20 mmol/l NADH, 150 to 250 mmol/l aspartate, and 10 to 20 mmol/l α-oxoglutarate and buffer 50 to 100 mmol/l pH 7.3 to 8.0.

As the buffer those buffer substances which are effective in the stated pH range are considered. Preferred are trisbuffer, trabuffer(triethanolamin) and phosphate buffer.

The inventively attained effect is shown in the FIGURE of the drawing enclosed. It shows the percentage reduction of the initial extinction against the storage time in hours for a known process or reagent by comparison with an inventive process or reagent. For the determination of the values in the FIGURE a reagent obtainable in the trade named "Monotest ® a ALAT-/ALT/GPT" for the determination of GPT made by Boehringer Mannheim GmbH was compared with the inventive reagent. The concentration in the test was as follows:
1200 U/l LDH,
0.180 mmol/l NADH,
15 mmol/l α-oxoglutarate,
500 mmol/l alanine,
100 mmol/l trisbuffer pH 7.5, The known reagent contained LDH from porcine hearts; the inventive reagent contained D-LDH of *lactobacillus leichmannii* DSM 2699.

In the FIGURE:
curve 1 shows the usual trade reagent at 25° C. (waterbath)
curve 2 shows the usual trade reagent at +4° C. (ice bath)
curve 3 shows the inventive reagent at 25° C. (waterbath)
curve 4 shows the inventive reagent at +4° C. (ice bath).

It can be seen that at 25° C. using the known reagent after about 34 hours, the whole of the NADH has disappeared, whereas with the inventive reagent even after 120 hours about 71% of the initial extinction is retained. The corresponding values at 4° C. and 120 hours storage time are for the known reagent 30% of residual extinction, for the invention reagent 90%. Similar results to those of porcine heart LDH are obtained when instead of the latter, L-LDH of *L. casei, L. xylosus, B. stearothermophilus* or *L. plantarum* is used.

Identical curves are obtained if instead of the above named conventional trade reagent for GPT determination, a corresponding trade reagent for GOT determination is used which is obtainable under the name "Monotest ® a ASAT/AST/GOT". The concentration in the test was:
600 U/l LDH
420 U/l MDH
0.180 mmol/l NADH
12 mmol/l α-oxoglutarate
240 mmol/l aspartate
80 mmol/l trisbuffer pH 7.8.

With this reagent a content of LDH is necessary because each sample contains endogenous pyruvate and as a rule, endogenous LDH as well. This leads to a slow reaction because of the slow break-up of the pyruvate, which takes place in a short period with the addition of excess and inventively used LDH.

This "side reaction" naturally also occurs in the same way in GPT determination, but here it is covered by the greater problem of the α-hydroxyglutarate dehydrogenase activity. The invention solves both these problems simultaneously.

It follows that the invention attains a multiplication of the storage stability.

A suitable enzyme preparation, for the invention, of *lactobacillus leichmannii* DSM 2699 can be prepared by the known process, e.g. using the process described in J. of General Microbiology (1970) 62, 243. This process is carried out basically as follows:

cell decomposition of lactobacillus suspended in 0.05M potassium phosphate buffer pH 7 by ultra-sonics. Centrifugation and rejection of the cell debris.

The raw microorganism extract thus obtained is brought to pH 5.5 with acetic acid, treated with protamine sulfate to 0.3% G/V and the deposit is centrifuged off. The residue is adjusted to pH 7 and the fraction precipitated with ammonium sulfate of between 50 and 85% saturation is extracted. This fraction is chromatographed in buffer ph 7 by a weak anion exchanger (DEAE-sephadex ® A 50) and is eluted with a NaCl gradient.

We obtain an LDH preparation with about 25% yield which is purified against the raw extract by a factor of 30 or more. This process is suitable also for other strains of the variety lactobacillus and leuconostoc, e.g. for *L. lactis* DSM 20072, *L. plantarum* DSM 20174, and *leuconostoc mesenteroides* DSM 20 193. For the pediococcus strains the process as in J. of Bacteriology vol. 121, p. 602 is used.

The examples below explain the invention further:

EXAMPLE 1 determination of GPT activity (version with phosphate buffer)
Sample material: serum, heparin or EDTA plasma,
reagents: (final concentration in the test)
phosphate buffer: 80 mmol/l pH 7.4,
L-alanine: 800 mmol/l pH 7.4,
LDH: ≦1200 U/l,
NADH: 0.18 mmol/l,
α-ketoglutarate: 18.0 mmol/l.
Determination method:
Wave length: Hg 365 nm, 340 nm or Hg 334 nm
Cuvette: 1 cm layer thickness
Temperature: 25° C.
Measurement against air (extinction reduction)
With photometers with analog display initial extinction compensation above 0.500 with cascade connection.

| Pipette into a cuvette | |
|---|---|
| reaction mixture (25° C.) | 2.5 ml |
| sample | 0.5 ml | mix. After about 1 minute, read the extinction and start the stopwatch at the same time. After exactly 1,2 and 3 minutes repeat the reading With extinction differences per minute (ΔE/min) of 0.06 to 0.08 (Hg 365) or 0.11 to 0.18 (Hg 334 and 340 nm) only the measurements of the first two minutes are considered (1 min. incubation and 2 min. measurement).

Find the average of the extinction differences per min. (ΔE/min) and insert them in the computation.
Computation:
The activity of the GPT in the sample is computed by:

$$U/l(25° C.) = 1765 \times \Delta E_{365} \text{ nm/min.}$$

$$U/l(25° C.) = 952 \times \Delta E_{340} \text{ nm/min.}$$

$$U/l(25° C.) = 971 \times \Delta E_{334} \text{ nm/min.}$$

EXAMPLE 2

Determination of the GOT activity (version with trisbuffer)
sample material: serum, heparin or EDTA plasma
reagents (final concentration in the test):
Tris-buffer: 100 mmol/l pH 7.5, NADH: 0.18 mmol/l pH 7.5,
MDH: 600 U/l,
LDH: 1200 U/l,
α-ketoglutarate: 12 mmol/l,
L-aspartate: 200 mmol/l.

Determination method:
Wave length Hg 365 nm, 340 nm or 334 nm
Cuvette: 1 cm layer thickness
measuring temperature: 25° C.
measurement against air (extinction reduction)

| Reagent solution (25° C.) | 2.5 ml |
|---|---|
| sample | 0.5 ml | mix, pour solution into a cuvette. After about 1 min., read off extinction and start the stopwatch at the same time. After exactly 1, 2 and 3 min. repeat the reading.

Form the average value of the extinction differences per min. and use it in the computation.

Computation:
The activity of the GOT in the sample should be taken from the table or computed as follows:

$$U/l(25° C.) = 2059 \times \Delta E_{365} \text{ nm/min}$$

$$U/l(25° C.) = 1111 \times \Delta E_{340} \text{ nm/min}$$

$$U/l(25° C.) = 1133 \times \Delta E_{334} \text{ nm/min.}$$

I claim:

1. A process for the determination of transaminase in a sample comprising contacting said transaminase containing sample with alpha-ketoglutaric acid and at least one amino acid to form glutamate and a transaminated alpha-ketoacid, further contacting said sample with D-lactate dehydrogenase obtained from lactic acid producing bacteria and NADH, said NADH reducing said transaminated alpha-keto acid product to an alpha oxyacid and being oxidized to NAD+, and determining the type of alpha oxyacid produced or measuring the rate of formation of NAD+ or alpha oxyacid to determine the type of transaminase or amount of transaminase present.

2. A process as in claim 1, wherein said transaminase is glutamate-pyruvate-transaminase, and said amino acid is alanine.

3. A process as in claim 1 wherein said transaminase is glutamate-oxalacetate-transaminase, and said amino acid is aspartate, wherein said process further comprises adding malate dehydrogenase to said sample.

4. A process as in claim 1, wherein said D-lactate dehydrogenase is obtained from bacteria selected from the group consisting of Lactobacillus, Pediococcus, and Leuconostoc bacteria.

5. A process as in claim 4, wherein said bacteria is selected from the group consisting of *Lactobacillus lactis* DSM 20072, *Lactobacillus plantarum* DSM 20174, *Leuconostoc mesenteroides* DSM 20193, and *Pediococcus pentosaceus* DSM 20280.

6. Composition useful in determining the presence of a transaminase comprising D-lactate dehydrogenase obtained from a lactic acid producing bacteria, alpha-oxoglutarate, an amino acid selected from the group consisting of alanine and aspartate, NADH and a buffer at a pH from 6.5 to 8.5.

7. Composition of claim 6, further comprising malate dehydrogenase.

8. Composition of claim 6, wherein said amino acid is alanine and said transaminase is glutamate pyruvate transaminase.

9. Composition of claim 6, wherein said amino acid is aspartate and said transaminase is glutamate oxalacetate transaminase.

10. Composition of claim 8, comprising from 250 to 20,000 U/l D-lacetate dehydrogenase, from 2.5 to 100 mMol/l alpha-oxoglutarate, from 50 to 1,000 mMol/l alanine, from 0.1 to 0.25 mMol/l NADH, and from 10 to 500 mMol/l of a buffer of pH from 6.5 to 8.5.

11. Composition of claim 9 comprising from 250 to 20,000 U/l D-lactate dehydrogenase from 2.5 to 100 mMol/l of alpha-oxoglutarate, from 20 to 1,000 mMol/l aspartate, from 0.01 to 0.25 mMol/l NADH, from 100 to 20,000 U/l malate dehydrogenase, and from 10 to 500 mMol/l of a buffer of pH from 6.5 to 8.5.

12. Composition of claim 6, wherein said D-lacetate dehydrogenase is obtained from a bacteria selected from the group consisting of Lactobacillus, Pediococcus, and Leuconostoc bacteria.

13. Composition of claim 12, wherein said bacteria are selected from the group consisting of *Lactobacillus leichmanii* DSM 2699, *Lactobacillus lactis* DSM 20072, *Lactobacillus plantarum* DSM 20174, *Leuconostoc mensenteroides* DSM 20193, and *Pediococcus pentosaceus* DSM 20280.

* * * * *